United States Patent [19]

Herron et al.

[11] Patent Number: 5,245,551
[45] Date of Patent: Sep. 14, 1993

[54] METHOD OF DETERMINING EXTINCTION COEFFICIENT OF FLUORESCENT DYE AND PROTEIN CONCENTRATION OF DYE-PROTEIN CONJUGATE

[75] Inventors: James N. Herron; Ai-Ping Wei, both of Salt Lake City, Utah

[73] Assignee: University of Utah Research Foundation, Salt Lake City, Utah

[21] Appl. No.: 683,145

[22] Filed: Apr. 10, 1991

[51] Int. Cl.$^5$ .............................................. G06F 15/20
[52] U.S. Cl. .................................... 364/497; 364/498
[58] Field of Search ............................... 364/492, 498

[56] References Cited

U.S. PATENT DOCUMENTS 5,041,378 8/1991 Drummond et al. ........... 435/71.2 X
5,051,249 9/1991 Metcoff ................................... 424/9

OTHER PUBLICATIONS

Wessendorf et al: "A Spectrophotometric Method For Determination of Fluorophore-To-Protein Ratios in Conjugates of the Blue Fluorophore 7-Amino-4-methylcoumorin-3-acetic Acid (AMCA)"; The Journal of Histochemistry and Cytochemistry; vol. 38 No. 1, 1990; pp. 87-94.

Neter et al: "Applied Linear Regression Models"; Irwin Inc.; ISBN 0-256-07068-7; 1989 pp. xiii, 225-236.

Beebe et al: "An Introduction to Multivariate Calibration and Analysis"; Analytical Chemistry, vol. 59 No. 17, Sep. 1, 1987; pp. 1007A-1017A.

Gemperline et al: "Background Correction in Multicomponent Spectroscopic Analysis Using Target Transformation Factor Analysis"; Applied Spectroscopy; vol. 41, No. 3; 1987 pp. 454-459.

I. C. McKay et al., "A comparison of Fluorescein Isothiocyanate and Liassamine Rhodamine (RB 200) As Labels for Antibody in the Fluorescent Antibody Technique", Immunology 1981, 43, 591-602.

P. L. Khanna, "Fluorescence Energy Transfer Immunoassays", Plenum Press, 1988, pp. 211-229.

Primary Examiner—Edward R. Cosimano
Attorney, Agent, or Firm—Richard P. Fennelly; Louis A. Morris

[57] ABSTRACT

The extinction coefficient of fluorescent dyes in donor-acceptor energy transfer processes is determined for dye-protein conjugates by forming short polypeptide fragment-dye conjugates and measuring the change in ultraviolet light absorbance of the conjugates with changing concentration. The protein concentration is determined by comparing the absorption spectrum of a conjugate of donor dye, acceptor dye, and protein with the individual components thereof using a multiple linear regression technique based on the following model:

$$A_{p-d} = \alpha \cdot A_p + \beta \cdot A_d + \epsilon$$

where, $A_{p-d}$, $A_p$, $A_d$ are the absorption spectra of the dye-protein conjugate, the protein alone, and the dye-polypeptide compound, respectively, $\alpha$, $\beta$ are the regression coefficients to be determined, and $\epsilon$ is the error term.

4 Claims, 1 Drawing Sheet

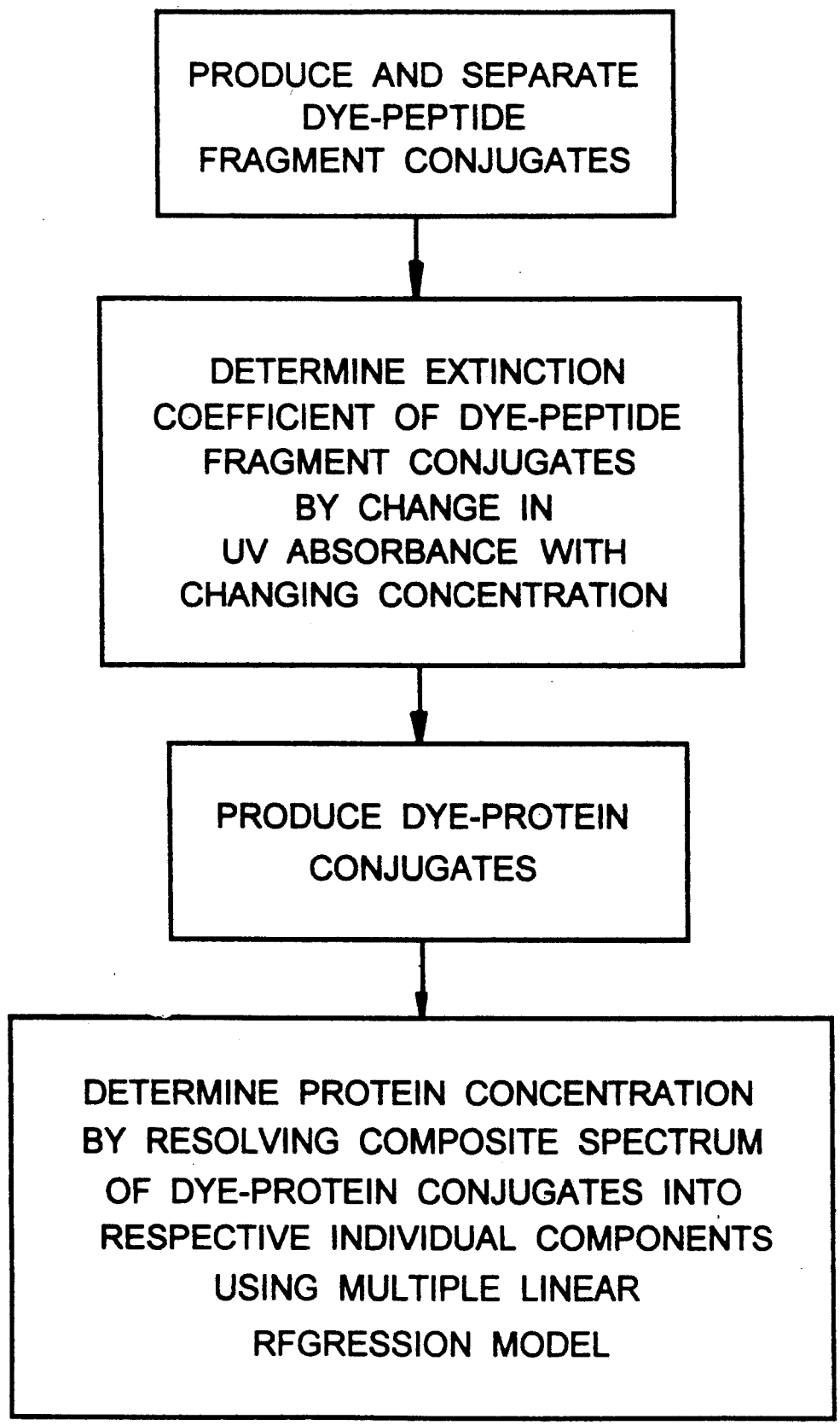

METHOD OF DETERMINING EXTINCTION COEFFICIENT OF FLUORESCENT DYE AND PROTEIN CONCENTRATION OF DYE-PROTEIN CONJUGATE

BACKGROUND OF THE INVENTION

Fluorescent energy transfer is one mechanism which has been proposed for use in biosensor applications. In selecting optimum donor-acceptor dye pairs a number of the following criteria should be met: 1) low overlap between the absorption spectra of donor and acceptor so that the direct excitation of the acceptor by the laser line is minimal: 2) high overlap between the emission spectra of donor and absorption spectra of acceptor so that the energy transfer efficiency is maximal; 3) good separation between the emission maxima of the donor and acceptor so that the ratio of the two intensities can be taken; 4) the donor should be able to be excited with a laser; 5) the fluorescence maxima of both donor and acceptor should be at a wavelength higher than serum fluorescence; 6) both donor and acceptor should have high extinction coefficients and high fluorescence quantum yields to ensure maximum sensitivity.

In order to select optimum donor-acceptor pairs and properly characterize their fluorescence properties various aspects of the pairs and their interactions with proteins (e.g., antibodies and antigens) need to be considered including such issues as: 1) energy transfer properties in solution; 2) spectral separation to determine the energy transfer efficiency; 3) other interactions between dyes besides energy transfer; 4) better methods to determine the degree of labeling; 5) calculation of the characteristic distance for all the potential donor-acceptor pairs; 6) fluorescence lifetimes of individual donors and acceptors, as well as the donor-acceptor pairs.

In order to quantitate the degree of labeling of immunoglobulin G (IgG), for example, with fluorescent dyes, it is important to use an accurate analytical method.

Techniques generally used in the literature are based on the assumption that dyes have the same spectra properties before and after conjugation to the protein. For example, McKay et al. described two formula to calculate the degree of labeling of gamma globulin with fluorescein and rhodamine (I. C. McKay, D. Forman, and R. G. White, 1981 Immunology, 43, 591–602). They stated clearly that "no allowance has been made for any changes that may take place in the ratio of $A_{280}/A_{495}$ on conjugation with protein". In determining the dye-to-protein ratio, Khanna calculated the protein content of the conjugates "from absorbance at 280 nm after subtracting the contribution due to free dye at this wavelength". (P. L. Khanna, 1988, in Nonisotopic Immunoassay, T. T. Ngo, eds., 211–229, plenum Press, New York). This procedure apparently assumes the spectra of conjugated dye is the same as the free dye. Recently, Wessendorf et al. developed a spectrophotometric method to determine the fluorophore-to-protein ratio in conjugates of 7-amino-4-methylcoumarin-3-acetic acid (AMCA) with mouse IgG. (M. W. Wessendorf et al. 1990, J. Histochemistry and Cytochemistry, 38, 87–94). They studied the effect of conjugation of the spectral properties of the dye by conjugating AMCA to the $\epsilon$-amino group of $N^{\alpha}$-acetyl lysine. The result was incorporated into the calculation procedure for the AMCA-to-protein ratio. This work is a significant improvement over the existing procedures. However, the model compound used in their study was a single amino acid, $N^{\alpha}$-acetyl lysine, which is different from a protein. In addition, the conjugation of dyes to the $\alpha$-amino groups was intentionally blocked by the use of acetylated lysine.

It has long been known that the $\alpha$-amino terminus exhibits a lower $pK_a$ than the $\epsilon$-amino side chain of lysine, and also that the $pK_a$ of the $\alpha$-amino terminus tends to decrease with increasing length of the polypeptide chain. Thus, an oligopeptide is a much better model for both the $\alpha$-amino and the $\epsilon$-amino groups than an acetylated amino acid. Furthermore, Wessendorf et al. did not apply multiple linear regression to analyze their data. More importantly, the dye they used had an emission maxima at 350 nm which is of little practical use for biosensor applications that involve blood serum because of the severe interference from serum fluorescence at this wavelength.

The procedure described for this invention, however, has major advantages over the existing methods because it involves the use of a polypeptide as a model compound to mimic the protein-dye reaction. Moreover, the dyes studied in regard to the present invention are fluorescein and their derivatives which are widely used in biosensor applications.

DESCRIPTION OF DRAWING

The Drawing, which forms a portion of the instant specification, is a flow diagram for the method of this invention.

DESCRIPTION OF THE INVENTION

The degree of labeling of fluorescent dye-protein conjugates involves accurate determination of both protein and dye concentrations in the form of conjugates. The procedure described in this invention includes two major aspects.

First, according to Beer's law dye concentration can be conveniently determined by its absorption at a certain wavelength using its extinction coefficient at this wavelength. In order to obtain an accurate extinction coefficient for a dye-protein conjugate in accordance with the present invention, a composition containing the dye molecules of interest is mixed with a composition comprising polypeptide fragments to achieve the attachment of such dye molecules to a portion of the polypeptide fragments to yield a dye-peptide fragment conjugate. The polypeptide fragment used is a "short" peptide containing up to about 12 amino acid units, for example, from about 3 to 10 amino acid units. A representative fragment which can be used contains three glycine units.

The resulting conjugates formed can be treated with appropriate separation techniques, e.g., high pressure liquid chromatography, to yield a series of compositions which, when exposed to a set wavelength of light, allow for the appropriate graphing of maximum absorbance at that wavelength for each concentration. The slope of the resulting plot is the extinction coefficient.

Second, the protein concentration is usually measured according to Beer's law by its absorption in the UV region, or by the Lowrry-Biuret methods. However, the presence of dyes interferes severely with these protein determination procedures. Therefore, some alternative method is needed for accurate protein determination.

In accordance with the present invention the composite visible ultraviolet (UV-VIS) absorption spectra of the dye-protein conjugates were resolved into its individual components using the following multiple linear regression model:

$$A_{p-d} = \alpha \cdot A_p + \beta \cdot A_d + \epsilon$$

where, $A_{p-d}$, $A_p$, $A_d$ are the absorption spectra of the dye-protein conjugate, protein alone, and the dye-polypeptide compound, respectively, $\alpha$ and $\beta$ are the regression coefficients to be determined, and $\epsilon$ is the error term which is usually under 2%. Moreover, the coefficient of determination (>0.99) also indicates that the model equation given above produces an excellent fit with experimental results.

The foregoing invention is further illustrated by the Examples which follow.

EXAMPLE

Initially, 5-, 6-carboxyltetramethyl rhodamine, succinimidyl ester (Molecular Probes, Inc., Eugene, Oreg.) was reacted with the short peptide, triglycine ($Gly_3$), in 50 mM phosphate buffer, pH 7.7, for about 24 hours at room temperature. The rhodamine-triglycine conjugates (T-$Gly_3$) were separated from the unreacted reactants on a $C_{18}$ reversed phase HPLC system (Waters, San Francisco, Calif.) using 80% acetonitrile and 20% $H_2O$ (pH 7) as the mobile phase. The conjugate was then lyophilized and weighed. The UV-VIS absorption spectra of the conjugate at several concentrations in 50 mM phosphate buffer, pH 7.7 was measured. The result is summarized below:

| Concentration, mg/ml (C) | Absorbance at 552 nm ($A_{552}$) |
|---|---|
| 0.0215 | 1.9022 |
| 0.0107 | 0.9734 |
| 0.0021 | 0.2037 |
| 0.0011 | 0.1016 |
| 0.0002 | 0.0208 |
| 0.0001 | 0.0104 |
| 0.0000 | 0.0022 |

When $A_{552}$ was plotted against molar concentration, a linear line was obtained. The molar extinction coefficient, determined from the slope, was 58810.26 ($cm^{-1} \cdot M^{-1}$).

In a second step, 5-, 6-carboxyltetramethyl rhodamine, succinimidyl ester was reacted with mouse immunoglobulins (Cappel, Organon Teknika Corporation) in 50 mM phosphate buffer, pH 7.7, for about 12 hours at room temperature. The labeled proteins were separated from unreacted dyes on a PD-10 gel filtration chromatography column (Pharmacia LKB, Piscataway, N.J.). The UV-VIS spectra of these tetramethylrhodamine-IgG (T-IgG) conjugates was measured.

In a third step, the complex spectra of the T-IgG conjugate was fitted with the spectra of T-$Gly_3$ and that of IgG according to the model given above ($A_{p-d} = \alpha \cdot A_p + \beta \cdot A_d + \epsilon$) for wavelengths ranging from 250 nm to 650 nm. The software used was StatWorks ™ (Cricket Software Inc., Philadelphia, Pa.). For the particular conjugate in this Example the following result was obtained:

$$A_{T-IgG} = 0.3847 \cdot A_{IgG} + 0.6222 \cdot A_{T-(Gly3)}$$

The error of fit was 1.6% and the coefficient of determination was 0.984.

The spectrum of T-IgG, fitted spectrum, contribution of T-$Gly_3$ and IgG are summarized in the following Table. In the actual analysis, 151 data points (wavelength interval=1 nm) were used, although intervals of 10 nm are listed below for the sake of space. The degree of labeling can be calculated, in principle, from the absorbance and extinction coefficient at any wavelength. In this particular Example we did the calculation which follows.

The content of IgG was determined from the absorbance at 278 nm. In the above equation, $A_{IgG}$ (278 nm)=0.201, the contribution of IgG in the conjugate was $A_{278} = 0.3847 \times 0.201 = 0.0779$. Using the molecular weight of 150,000 daltons and an extinction coefficient of $\epsilon_{1mg/ml}$ (278 nm)=1.4, the content of IgG was calculated to be $3.7 \times 10^{-7}$ M.

The rhodamine concentration was determined from its absorbance at 552 nm using the extinction coefficient obtained previously. $A_{T-Gly3}$ (552 nm)=0.204, the contribution of the rhodamine was $A_{552} = 0.6222 \times 0.204 = 0.127$. Using the extinction coefficient of $\epsilon_{1M}$(552 nm)=58810.26, the content of rhodamine was calculated to be $2.16 \times 10^{-6}$ M.

The degree of labeling was therefore 5.8 rhodamine per protein molecule.

TABLE*

| Wavelength (nm) | Absorbance of T-IgG | Fitted Value | Contribution of T-$GL_{y3}$ | Contribution of IgG |
|---|---|---|---|---|
| 250 | 0.0793 | 0.0716 | 0.0077 | 0.0295 |
| 260 | 0.0857 | 0.0804 | 0.0053 | 0.0418 |
| 270 | 0.0900 | 0.0892 | 0.0008 | 0.0656 |
| 280 | 0.0989 | 0.1023 | −0.0034 | 0.0771 |
| 290 | 0.0735 | 0.0742 | −0.0007 | 0.0506 |
| 300 | 0.0347 | 0.0338 | 0.0009 | 0.0110 |
| 310 | 0.0241 | 0.0219 | 0.0022 | 0.0017 |
| 320 | 0.0122 | 0.0104 | 0.0018 | 0.0008 |
| 330 | 0.0043 | 0.0074 | −0.0031 | 0.0006 |
| 340 | 0.0027 | 0.0098 | −0.0071 | 0.0006 |
| 350 | 0.0055 | 0.0134 | −0.0079 | 0.0004 |
| 360 | 0.0075 | 0.0114 | −0.0039 | 0.0004 |
| 370 | 0.0008 | 0.0054 | −0.0046 | 0.0003 |
| 380 | −0.0033 | 0.0046 | −0.0079 | 0.0007 |
| 390 | −0.0022 | 0.0043 | −0.0065 | 0.0002 |
| 400 | −0.0018 | 0.0050 | −0.0068 | 0.0003 |

*Negative values are due to data acquisition error of the instrument.

The linear regression model can be used for wavelengths of from about 250 nm to about 650 nm.

We claim:

1. A method of determining the extinction coefficient of a fluorescent dye when it is attached to a protein and the protein concentration thereof which comprises:

(a) mixing a composition comprising dye molecules with a composition comprising peptide fragments to achieve the attachment of a portion of the dye molecules to a portion of the peptide fragments so as to produce dye-peptide fragment conjugates and separating the conjugates therefrom;

(b) determining the extinction coefficient of the dye-peptide fragment conjugates by measuring the change in visible ultraviolet light absorbance of the conjugates with changing concentration;

(c) producing dye-protein conjugates and determining the protein concentration in the conjugates by resolving the composite spectrum of the dye-protein conjugates into their respective individual components using multiple linear regression according to the model:

$$A_{p-d} = \alpha \cdot A_p + \beta \cdot A_d + \epsilon$$

where, $A_{p-d}$, $A_p$, $A_d$ are the absorption spectra of the dye-protein conjugate, protein alone, and the dye-peptide fragment, respectively, $\alpha$ and $\beta$ are the regression coefficients to be determined, and $\epsilon$ is the error term.

2. A method as claimed in claim 1 wherein the linear regression model is used for wavelengths of from about 250 nm to about 650 nm.

3. A method as claimed in claim 1 wherein the peptide fragments contain up to about 12 amino acid units.

4. A method as claimed in claim 3 wherein the linear regression model is used for wavelengths of from about 250 nm to about 650 nm.

* * * * *